United States Patent [19]
Kee

[11] Patent Number: 6,070,582
[45] Date of Patent: Jun. 6, 2000

[54] SUCTION CONTROL VALVE

[75] Inventor: Kok-Hiong Kee, Johor, Malaysia

[73] Assignee: Sherwood Services, AG, Schaffhausen, Switzerland

[21] Appl. No.: 08/926,886

[22] Filed: Sep. 10, 1997

Related U.S. Application Data

[60] Provisional application No. 60/025,868, Sep. 10, 1996.
[51] Int. Cl.[7] .......................... A61M 16/00; A61M 1/00; E03B 1/00
[52] U.S. Cl. ...................... 128/207.16; 137/381; 604/119
[58] Field of Search ...................... 128/207.16; 604/163, 604/171, 119; 137/381

[56] References Cited

U.S. PATENT DOCUMENTS

| | | | |
|---|---|---|---|
| 975,645 | 11/1910 | Sherburne . | |
| 1,088,817 | 3/1914 | Graham . | |
| 1,214,267 | 1/1917 | Block . | |
| 2,376,971 | 5/1945 | Kleit | 128/207 |
| 2,638,096 | 5/1953 | Waldhaus | 128/348 |
| 2,791,217 | 5/1957 | Iskander | 128/203 |
| 3,012,752 | 12/1961 | Buck | 251/309 |
| 3,081,770 | 3/1963 | Hunter | 128/221 |
| 3,335,727 | 8/1967 | Spoto | 128/276 |
| 3,385,324 | 5/1968 | Wolf et al. | 137/636.4 |
| 3,395,705 | 8/1968 | Hamilton | 128/276 |
| 3,818,539 | 6/1974 | Fortune | 15/341 |
| 3,844,275 | 10/1974 | Elliot | 600/343 |
| 3,991,762 | 11/1976 | Radford | 128/276 |
| 4,011,828 | 3/1977 | Black | 116/70 |
| 4,291,691 | 9/1981 | Cabal et al. | 128/204.18 |
| 4,325,377 | 4/1982 | Boebel | 128/326 |
| 4,334,538 | 6/1982 | Juhn | 128/276 |
| 4,346,702 | 8/1982 | Kubota | 128/207.14 |
| 4,569,344 | 2/1986 | Palmer | 128/207.16 |
| 4,648,868 | 3/1987 | Hardwick et al. | 604/32 |
| 4,662,871 | 5/1987 | Rafelson | 604/119 |
| 4,759,364 | 7/1988 | Boebel | 128/326 |
| 4,792,327 | 12/1988 | Swartz | 604/22 |
| 4,818,227 | 4/1989 | Krueger | 433/27 |
| 4,856,564 | 8/1989 | Obal | 141/95 |
| 4,872,579 | 10/1989 | Palmer | 128/205.19 |
| 5,015,249 | 5/1991 | Nakao et al. | 606/142 |
| 5,083,561 | 1/1992 | Russo | 128/207.16 |
| 5,139,018 | 8/1992 | Brodsky et al. | 128/207.14 |
| 5,163,945 | 11/1992 | Ortiz et al. | 606/142 |
| 5,335,655 | 8/1994 | Kee | 128/207.16 |
| 5,337,780 | 8/1994 | Kee | 604/119 |
| 5,368,017 | 11/1994 | Sorenson et al. | 128/200.26 |
| 5,377,672 | 1/1995 | Kee | 128/207.16 |
| 5,496,287 | 3/1996 | Jinotti | 604/249 |
| 5,720,282 | 2/1998 | Wright | 128/203.12 |

*Primary Examiner*—John G. Weiss
*Assistant Examiner*—Todd M Martin
*Attorney, Agent, or Firm*—Mark S. Leonardo; Brown, Rudnick, Freed & Gesmer, P.C.

[57] ABSTRACT

A suction control valve is disclosed which includes a primary suction device access and an ancillary suction device access. The valve includes a valve core which is linearly movable between a first position in which the primary access is closed against suction pressure therethrough, to a second position in which the primary access is open to suction pressure therethrough. The valve also is rotatable from the first position to a third position to disable its linear movement and to open the ancillary access port. When the core is in the first position, atmospheric air can pass through the valve and into the suction pressure source in such a manner that a "hissing" auditory signal is generated, indicative of the presence of suction pressure within the valve. When the actuator is in the second or third positions, the "hissing" is prevented. The valve is easily assembled and adapted for gas sterilization.

9 Claims, 10 Drawing Sheets

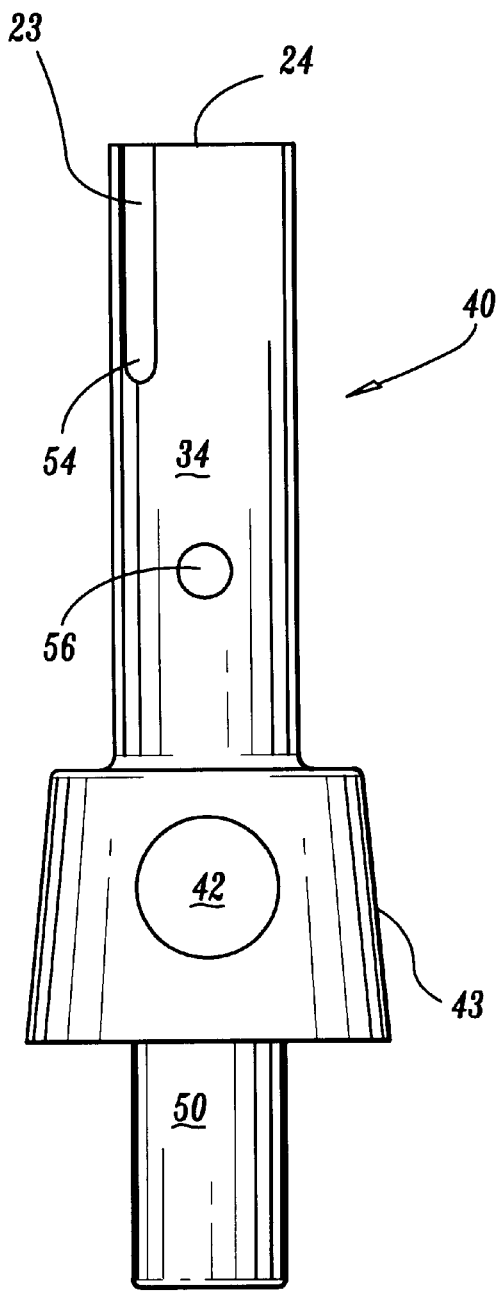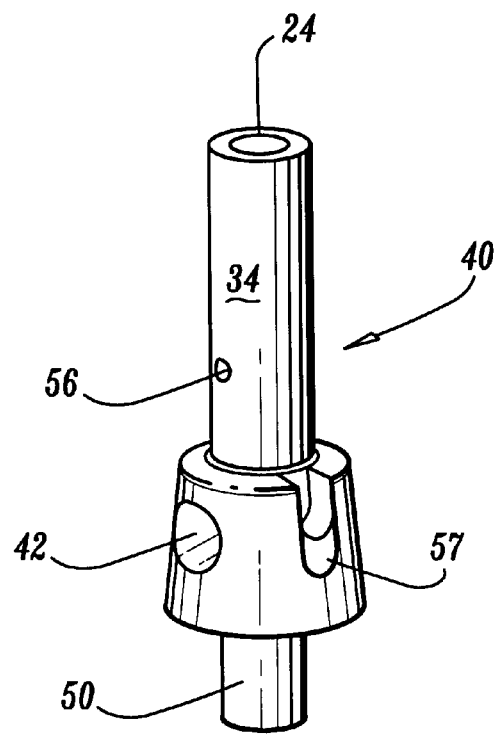
FIG. 9
FIG. 10

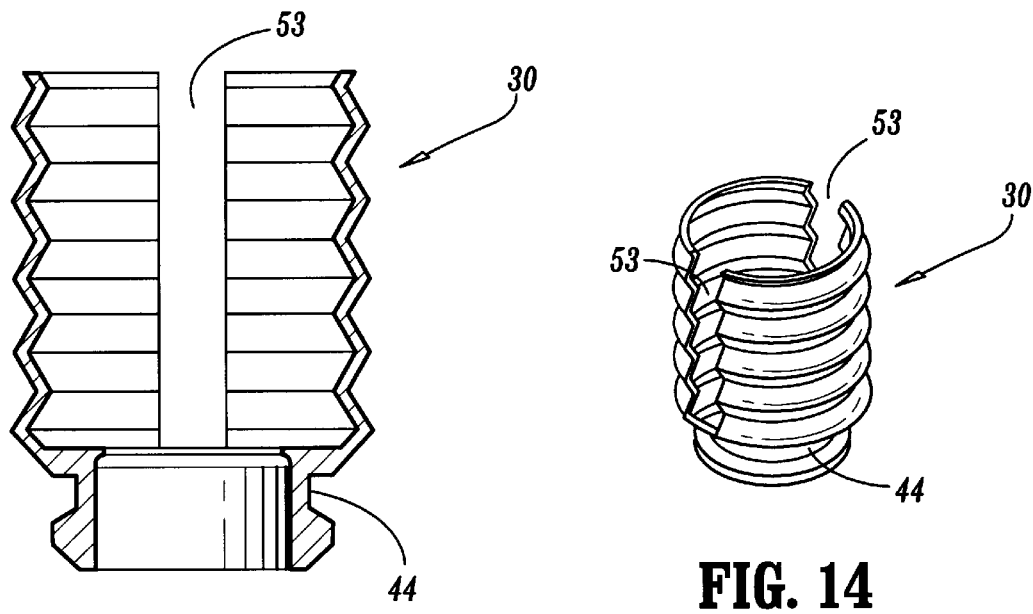
FIG. 13
FIG. 14
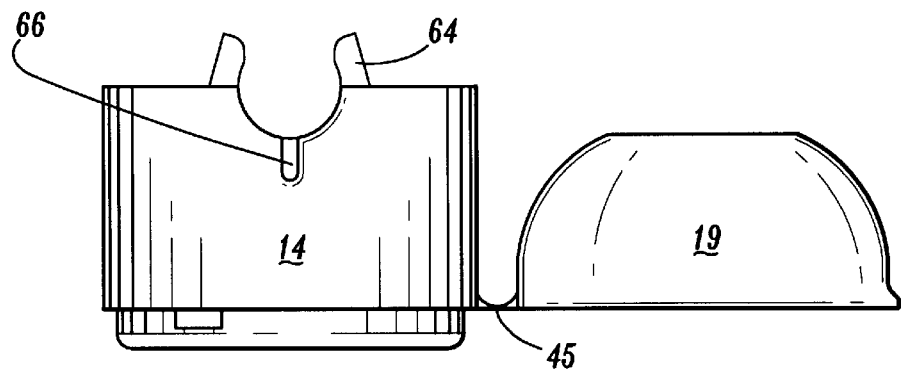
FIG. 15
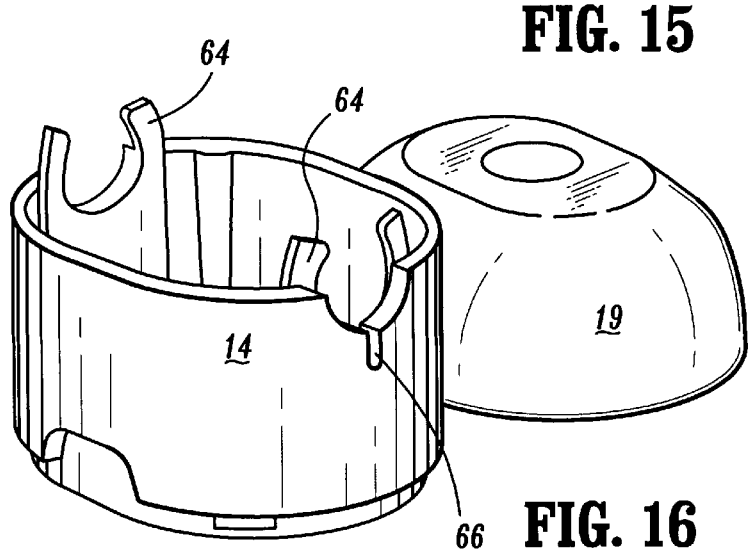
FIG. 16

SUCTION CONTROL VALVE

CROSS-REFERENCE TO RELATED APPLICATIONS

This Patent Application claims benefit of U.S. Provisional Application No. 60/025,868 filed Sep. 10, 1996, the contents of which are incorporated herein by reference in its entirety.

BACKGROUND OF THE INVENTION

1. Field of the Invention

This invention relates generally to fluid flow valving devices. More specifically, the present invention relates to a valve usable with a suction catheter. Even more specifically, the present invention relates to a suction control valve useable with suction catheters attachable to a respirator manifold of a respiratory system.

2. Prior Art

Respiratory systems for ventilation of critically ill patients are now commonly used in medical facilities. The purpose of the respiratory system is to assist the patient in maintaining adequate blood oxygenation levels without overtaxing the patient's heart and lungs. Typically, a prior art respiratory system includes a tracheal tube positioned either directly or through the nose or mouth into the trachea of a patient. The tracheal tube is connected to a manifold at one port position thereof, and a source of breathable gas is connected at a second port thereof.

While a patient is attached to a respiratory system, it is periodically necessary to remove fluid from the patient's trachea or lungs. In the past this procedure necessitated disconnections of the respirator system, either by removing the manifold or by opening a port thereof, and inserting a small diameter suction catheter down the tracheal tube and into the patient's trachea and lungs. The fluid was then suctioned from the patient and the suction catheter was removed and the respirator system reassembled. Because of the necessary interruption in respiratory support to perform this procedure, a patient's blood oxygen often dropped to an unacceptably low level during suctioning, even when other previously known breathing assistance efforts were simultaneously provided.

A known solution to the above problem has been to place an additional port on the respirator manifold which is adapted to receive a connector of a suction catheter device. A suction catheter device such as used with this type of respirator manifold is adapted to allow the suction catheter to remain positioned within the respirator manifold without the necessity of attachment or detachment thereof between uses, thereby avoiding substantial manifold pressure loss. The suction catheter device includes a sleeve which envelopes the suction catheter in order to prevent contamination of the suction catheter surface which must be repeatedly inserted into and removed from the patient's trachea and lungs. This type of suction catheter device allows continuous respiratory support of the patient during suctioning of fluid from the patient's trachea and lungs, and is commonly controlled by means of a valve located in fluid flow connection between the catheter and the suction source therefore. A valve of this type which is generally exemplary of the prior art is shown in U.S. Pat. No. 4,872,579 issued to Palmer. The Palmer valve selectively communicates vacuum pressure into the interior of a catheter tube when it is desired to evacuate respiratory fluids. It is normally biased to a closed position to prevent vacuum flow until the operator thereof initiates a manual displacement of a valve actuator to open the catheter tube to the vacuum source. The valve actuator is also designed to be rotatable relative to the remainder of the valve from a closed position to a locked position which prevents actuation of the valve actuator between uses.

Other suction catheter devices of this type include U.S. Pat. No. 5,335,655, U.S. Pat. No. 5,337,780, and U.S. Pat. No. 5,377,672 issued to Kee, the inventor of the present invention and commonly assigned herewith.

The above and other prior art valving devices however suffer from several drawbacks, including but not limited to, being manufactured of relatively numerous and expensive components which are difficult and expensive to assemble, and being made to a design which does not allow for complete gas sterilization of the device after its assembly due to inaccessible and trapped regions therein which cannot be reliably penetrated by the sterilization gas.

OBJECTS AND SUMMARY OF THE INVENTION

A principal object of the present invention is to provide a fluid flow valving device which is designed to provide the user with an easily assemblable manufacturing design.

Another principal object of the present invention is to provide a fluid flow valving device which allows for complete and reliable gas sterilization thereof after its assembly.

An additional object of the present invention is to provide a fluid flow valving device which is easily actuatable by the operator regardless of the level of suction drawn therethrough by a suction source to which it may be attached.

Another object of the present invention is to provide a fluid flow valving device designed with a locking and unlocking valve actuator which includes an auditory signaling means which informs the user of the locked or unlocked status of the valve.

A further object of the present invention is to provide a fluid flow valving device which is designed to allow attachment thereto of primary and ancillary devices such as a primary suction catheter device and an ancillary Yankauer suctioning device, which allows complete opening or closure of the primary device in isolation from the ancillary device, whereby the fluid flow valving device functions only as a connector of the ancillary device to the suction source and thus avoids any necessity of removing the fluid flow valving device from the suction source in order to attach the primary or ancillary device thereto, or to change from the use of one to the other.

These and other objects of the present invention are realized in a presently preferred embodiment thereof, described by way of example and not necessarily by way of limitation, which includes a suction control valve for controlling suction through a preferred primary device, shown for purposes of description as a suction catheter, and provides a connection port for an ancillary device such as a Yankauer suction wand.

The valve includes a main body forming a fluid flow passage therethrough and includes a valve core for opening and closing the fluid flow passage. The valve core is formed in an inverted cone shape and is normally biased to a position in which the fluid flow passage is closed to fluid flow therethrough. The valve core may be actuated by the operator thereof against the bias in order to open the fluid flow passage. The valve core may also be rotated relative to the valve body to a locked position in which it can no longer be actuated to cause fluid flow through the fluid flow passage. Tubular extensions for attachment of the valve to a suction source and to a primary device are included on each end of the fluid flow passage.

The valve also includes an ancillary device connection port positioned opposite the valve core which is normally closed with a flip top cap and can be opened to expose a connection port which is designed to receive an ancillary device such as a Yankauer suctioning wand therein. The port is placed in fluid flow connection with the fluid flow passage when the valve core is rotated to the locked position.

The valve is designed to ensure that each of its internal members has only one possible assembly orientation, and/or the elements are keyed to each other such that only properly oriented elements can be assembled to each other. Further, each internal element of the valve is designed such that when sterilization by gas sterilization is performed thereon, an open air channel exists to allow the gas to contact every internal surface during sterilization.

BRIEF DESCRIPTION OF THE DRAWINGS

FIG. 9 is a side view of the valve core as shown in FIG. 8 except rotated ninety degrees along its longitudinal axis;

FIG. 10 is a perspective view of the valve core of the fluid flow valving device of the present invention;

FIG. 13 is a cross-sectional view of the elastomeric spring portion of the fluid flow valving device formed in accordance with the principals of the present invention;

FIG. 14 is a perspective view of the elastomeric spring of FIG. 13;

FIG. 15 is a side view of the bottom, or flip cap portion of the housing of the fluid flow valving device formed in accordance with the principals of the present invention;

FIG. 16 is a perspective view of the bottom portion of the housing as shown in FIG. 15;

DETAILED DESCRIPTION OF THE PREFERRED EMBODIMENT

Figure 1:
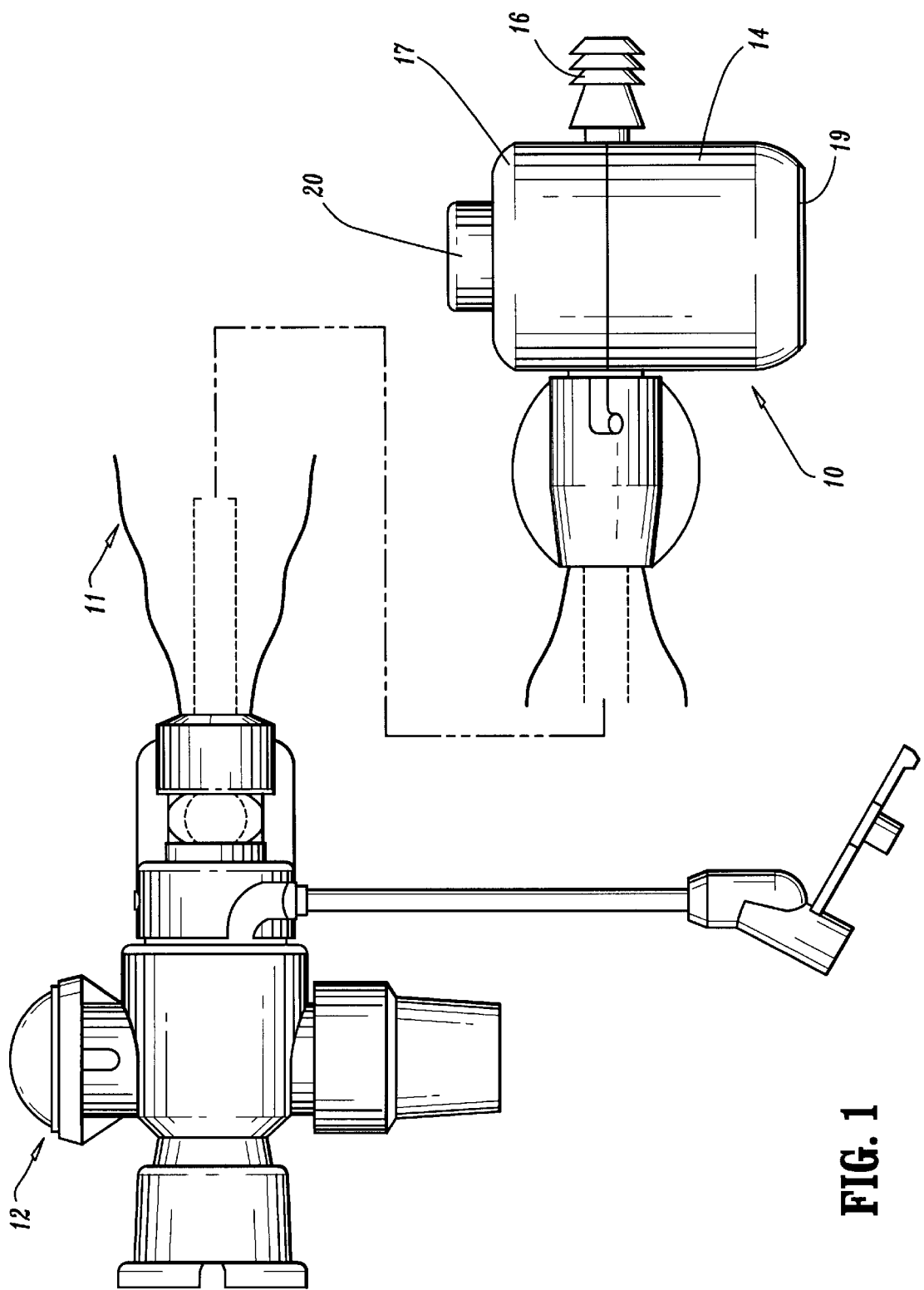
FIG. 1 shows a perspective view of a fluid flow valving device formed in accordance with the principals of the present invention attached to a suction catheter device designed for use with a respiratory support system.

As shown in the exemplary drawings for the purposes of illustration, an embodiment of a fluid flow valving device made in accordance with the principals of the present invention, referred to generally by the reference numeral 10, is provided for attachment to a suction source and a primary suctioning device and, when desired, to an ancillary suctioning device.

More specifically, as shown in FIG. 1, the suction control valve 10 is shown attached to a suction catheter device 11 which is adapted to be used in conjunction with a patient respiratory support system through attachment to a respirator manifold such as the manifold 12. The valve 10 is also attachable to a source of suction pressure by means of a suction tube or the like (not shown).

Figure 2:
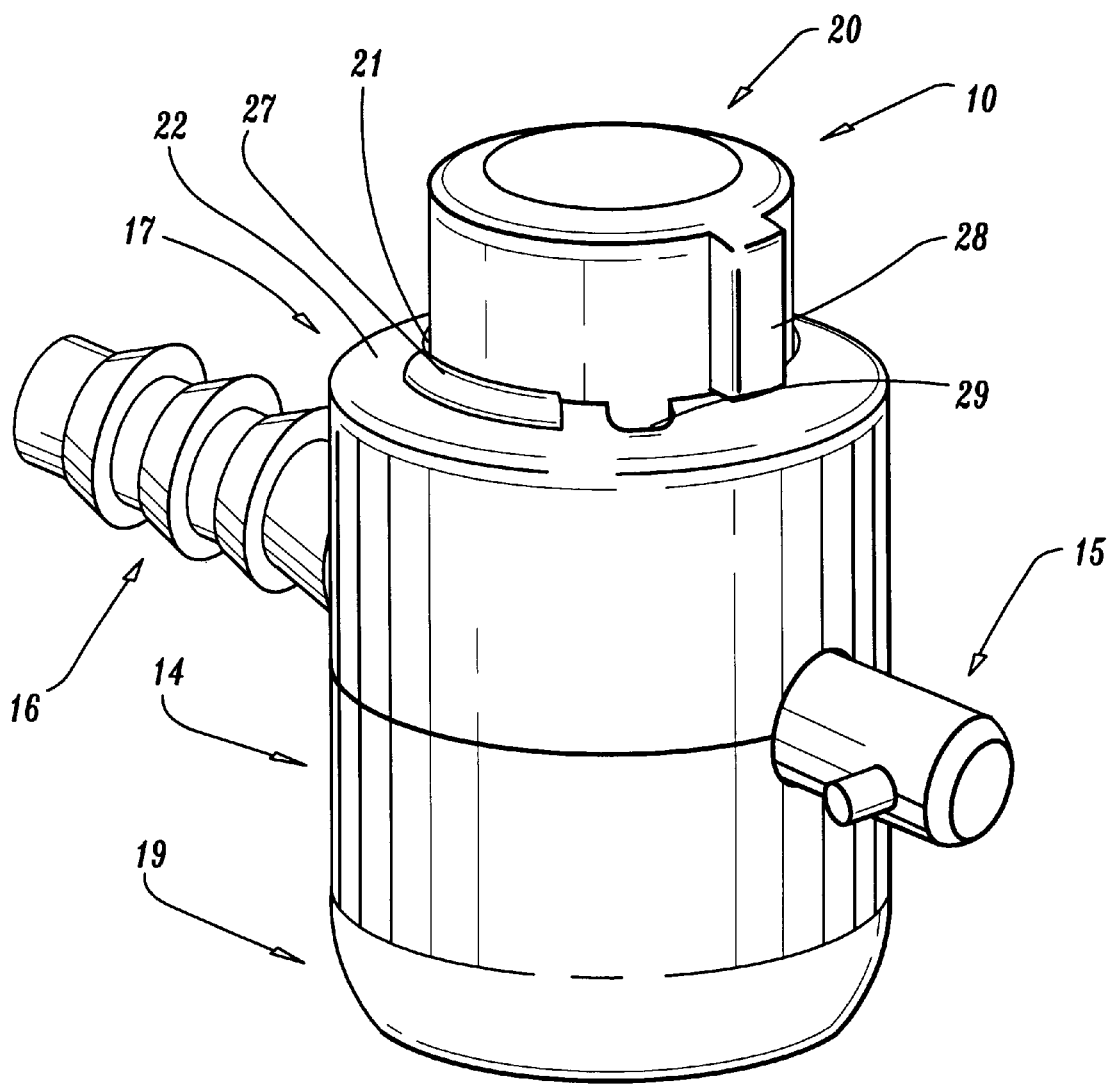
FIG. 2 is a perspective view of a fluid flow valving device formed in accordance with the principals of the present invention.
Figure 3:
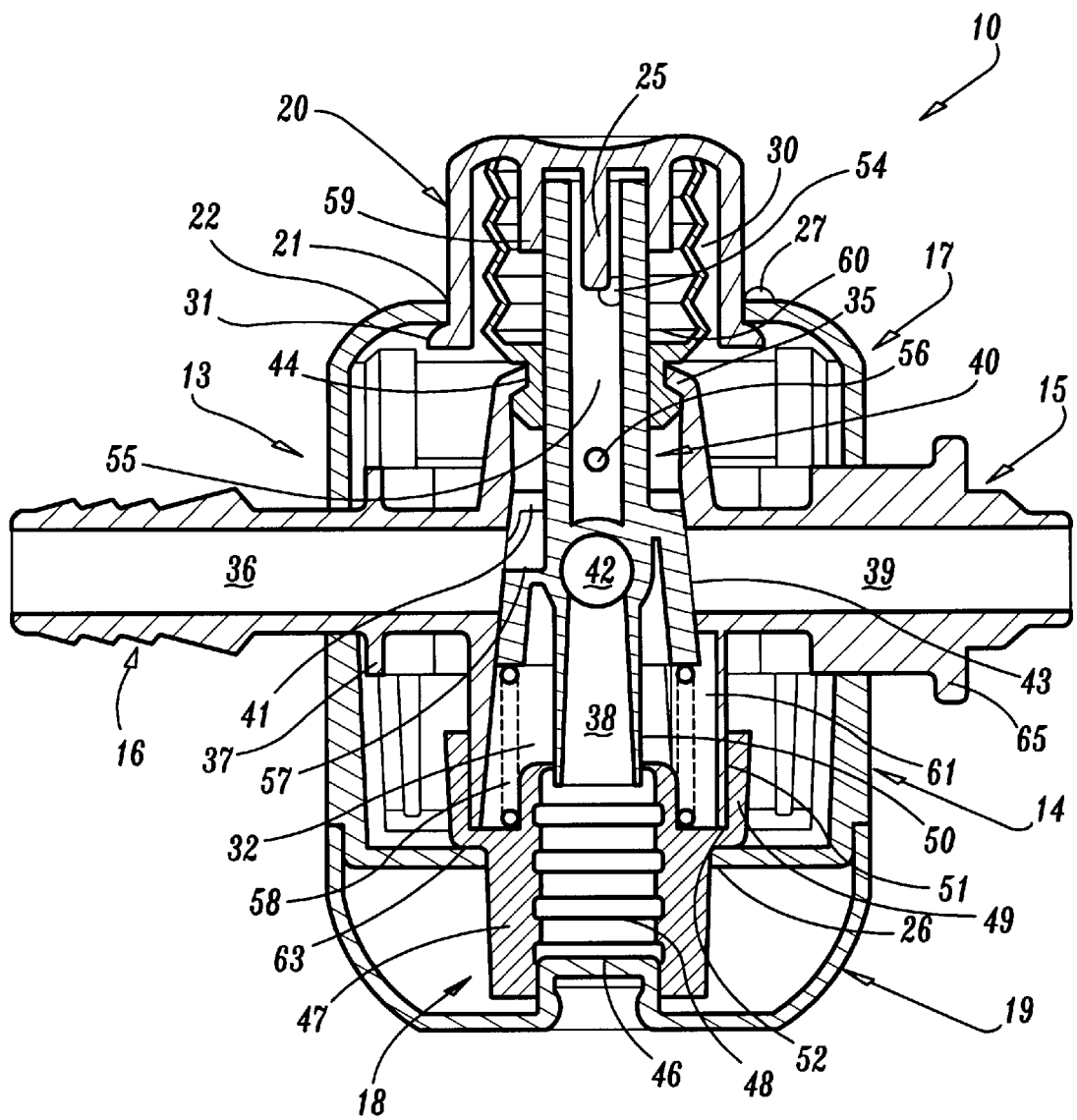
FIG. 3 is a cross-sectional view of the fluid flow valving device of FIG. 2, showing the valve in the open position.
Figure 4:
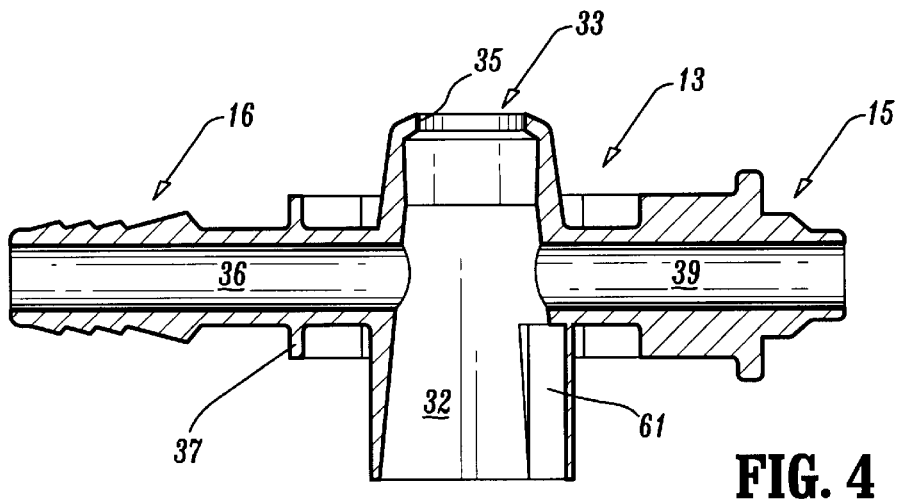
FIG. 4 is a cross-sectional view of the valve body of the fluid flow valving device of the present invention.
Figure 5:
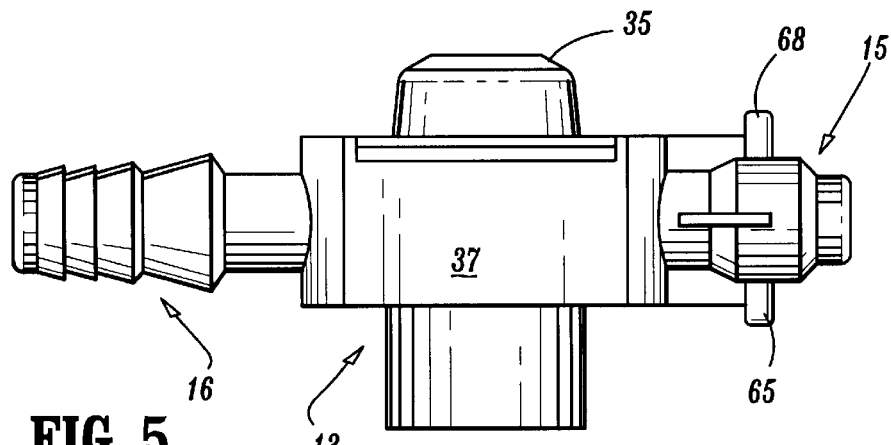
FIG. 5 is a side view of the valve body of the fluid flow valving device of the present invention.
Figure 6:
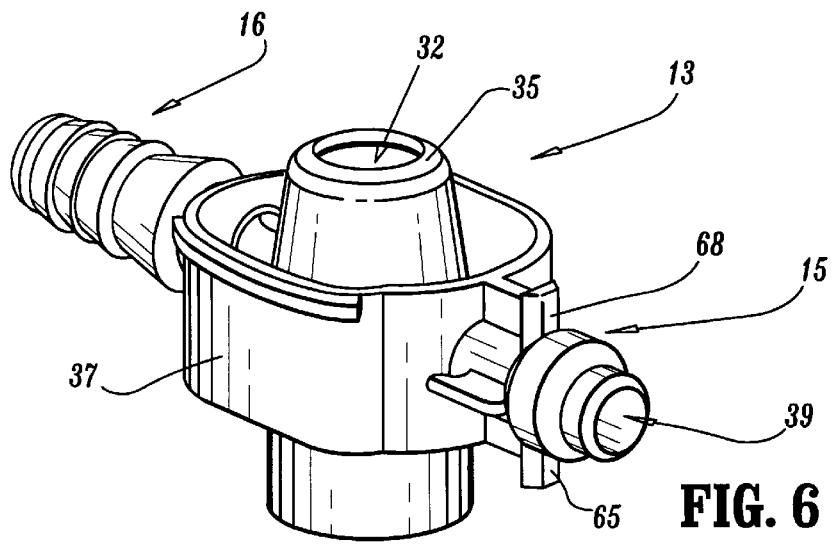
FIG. 6 is a perspective view of the valve body of the fluid flow valving device of the present invention.

As shown in FIGS. 2 and 3, the valve 10 of the present invention includes a valve body 13 having a primary device connector 15 extending outwardly therefrom in a radial direction and a suction source connector 16 extending in a radial direction opposite the primary device connector 15. A lower cap 14 surrounds the lower portion of the valve body 13 and includes an ancillary device connection port cover 19 hingedly attached thereto. The cover 19 has approximately the same diameter as the lower cap 14 and covers the access to the ancillary device connection port 18.

An upper cap 17 is connected to the top portion of the valve body 13 and mates with the lower cap 14. A portion of a button 20 extends from the interior of the upper cap 17 through the upper cap opening 21 and above the annular surface 22. The positioning of the button 20 on the valve 10 is intended to allow for ease of manipulation thereof in a single hand of the user. The valve 10 is sized so as to be easily placeable within a user's palm such that the user's thumb may rest comfortably on the button 20, with the user's fingers curling about the lower cap 14 and cover 19.

Referring now to FIGS. 3–6, the valve body 13 is formed generally into a hollow cylindrical shape and includes the primary device connector 15 and suction source connector 16 which are formed through the side wall 37 at diametrically opposed positions.

A cylindrical fluid flow channel, identified for simplicity of later explanation of operation of the valve 10 as channels 36 and 39, passes completely through the valve body 13. The channels 36 and 39 are oriented such that their longitudinal axis perpendicularly intersects with the longitudinal axis of the conical bore 32. The conical bore 32 is surrounded at its top opening 33 by an annularly shaped seat 35. The conical bore 32 also includes a vertical slot 61 formed therein which extends around the interior of the conical bore 32 a distance of ninety radial degrees. The vertical slot 61 receives the nub 62 (see FIG. 8) of the valve core 40 and thereby allows the valve core to rotate only through a ninety degree arc relative to the valve body 13.

As best shown in FIGS. 3 and 7–10, the valve core 40 rests within the conical bore 32, and is generally conical in shape to match the shape of the conical bore 32. The core 40 forms several channels therethrough which can be positioned for operation of the valve 10 by rotation of the core 40 relative to the body 13 in the manner as will be described below.

Figure 11:
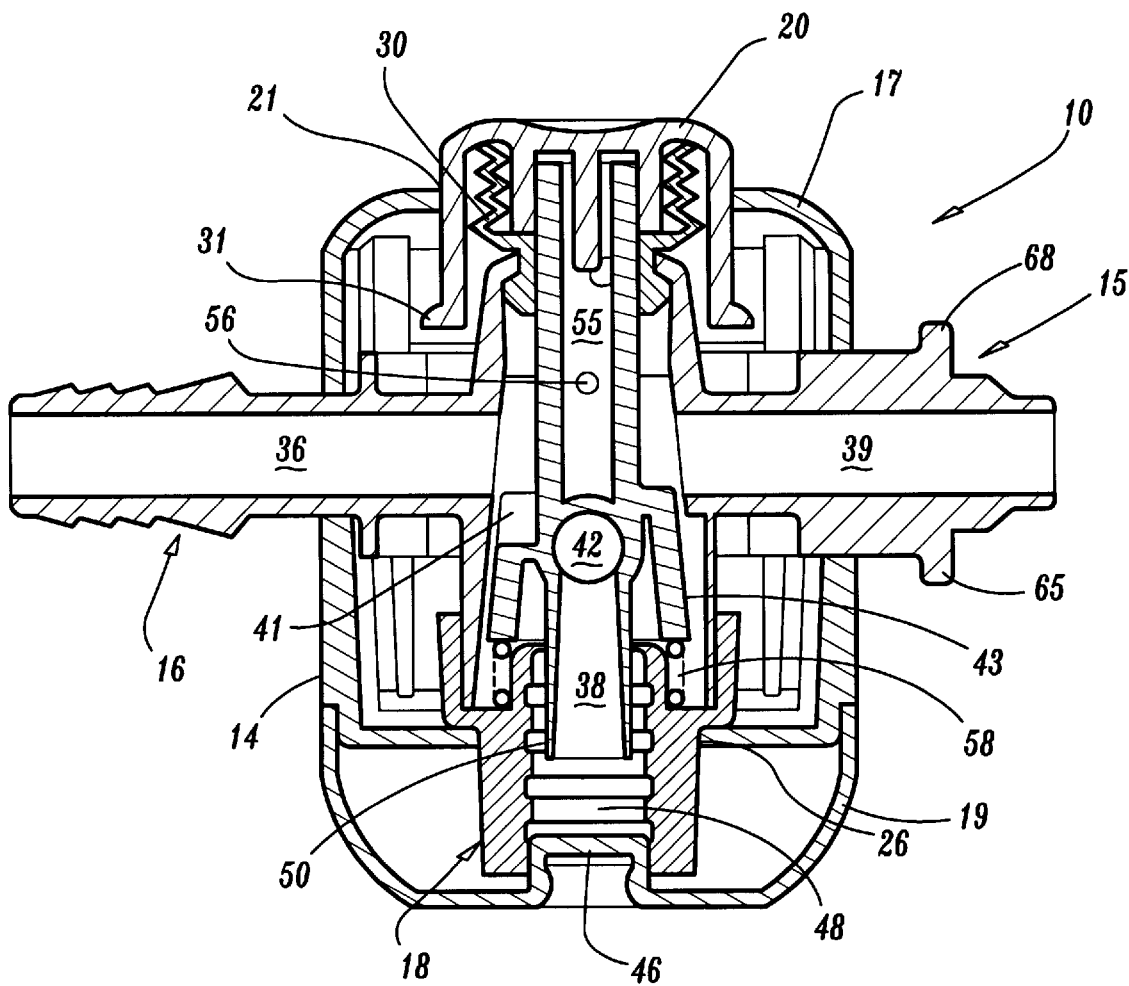
FIG. 11 is a cross-sectional view of the fluid flow valving device of the present invention, showing the valve in the actuated position.
Figure 12:
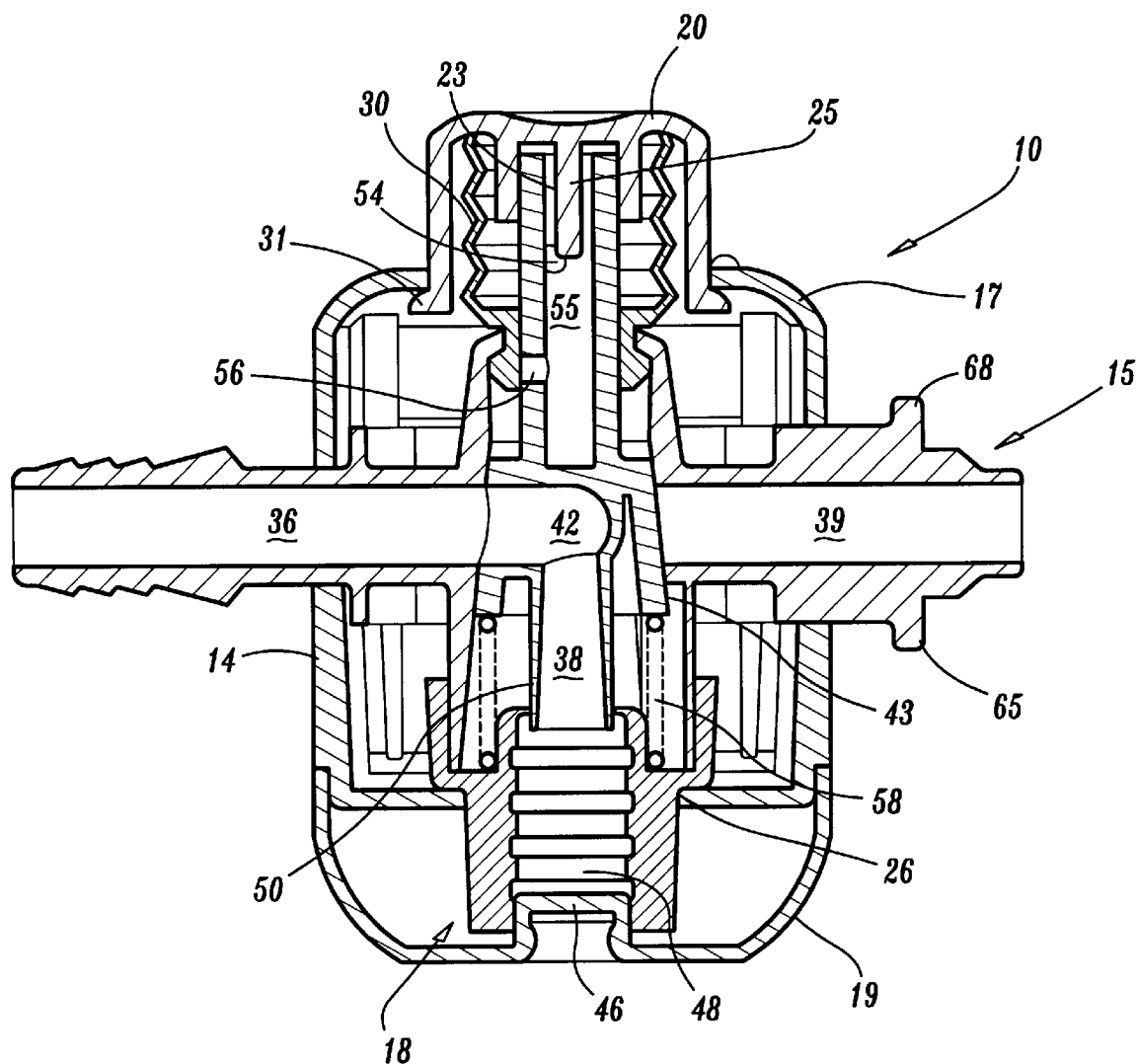
FIG. 12 is a cross-sectional view of the fluid flow valving device of the present invention, showing the valve in the locked position.

A primary fluid flow channel 41 is formed in the core 40 so as to be alignable with the fluid flow channel 36 in the body 13. An ancillary fluid flow channel 42 is also formed in the core 40 so as to be alignable with the channel 36. The ancillary fluid flow channel 42 is oriented in the core 40 approximately ninety rotational degrees around the circumference of the core 40 from the primary fluid flow channel 41. The relative positioning of the primary and ancillary fluid flow channels 41 and 42 respectively, allow positioning of the core 40 in a first or "open" position (shown in FIG. 3) in which the primary fluid flow channel 41 is rotationally oriented for fluid flow between channels 36 and 39 but out of vertical alignment therewith, a second or "actuated" position (as shown in FIG. 11) in which the primary fluid flow channel 41 is rotationally oriented and vertically aligned with channels 36 and 39, and a third or "locked" position (as shown in FIG. 12) in which the core 40 is rotated 90° to align the ancillary fluid flow channel 42 thereof between channel 36 and the secondary cylindrical fluid flow channel 38. The operation of the valve 10 with respect to each position of the core 40 will be explained in detail momentarily.

Figures 7, 8:
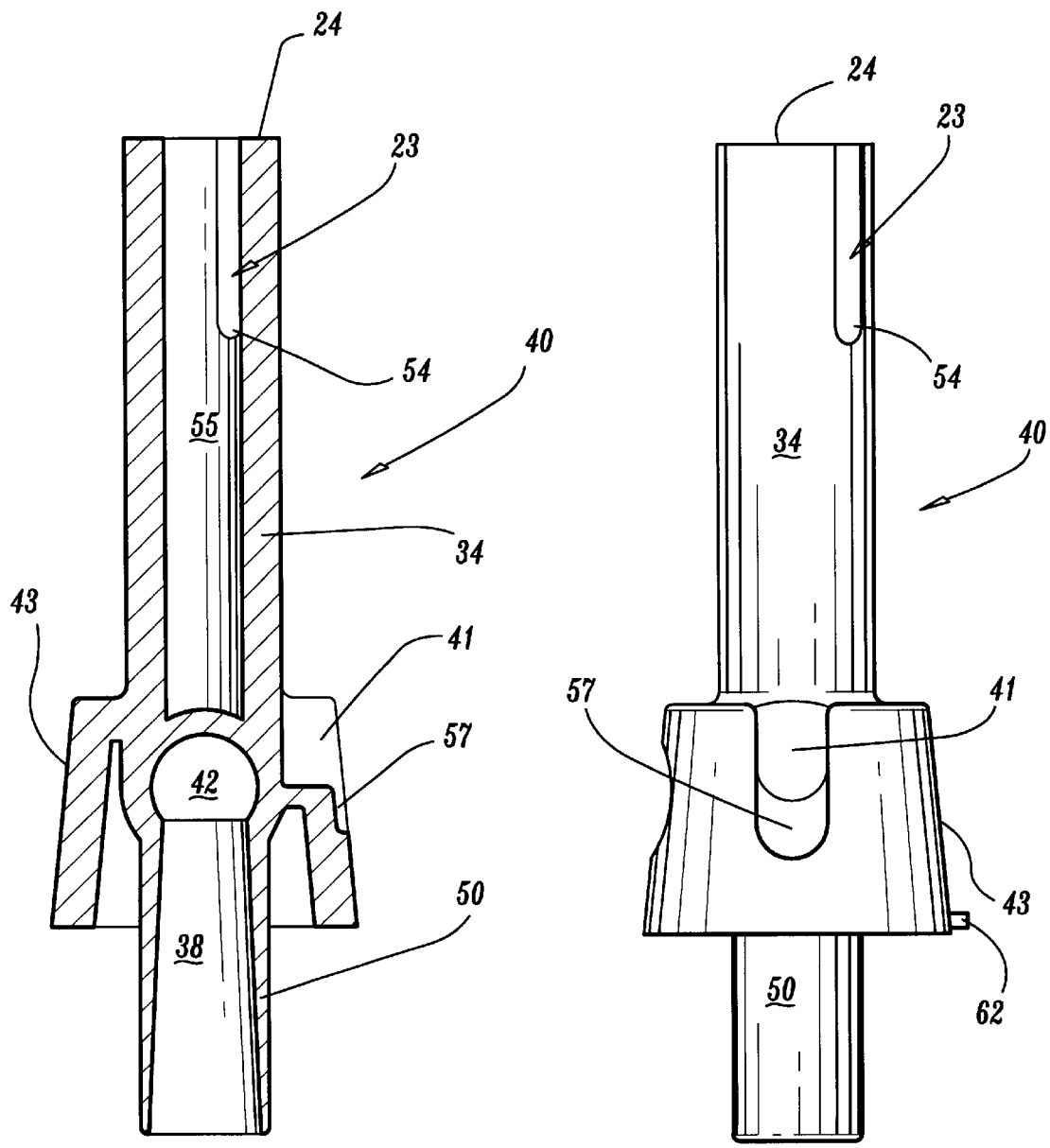
FIG. 7 is a cross-sectional view of the valve core of the fluid flow valving device of the present invention.
FIG. 8 is a side view of the valve core of the fluid flow valving device of the present invention.
Figure 19:
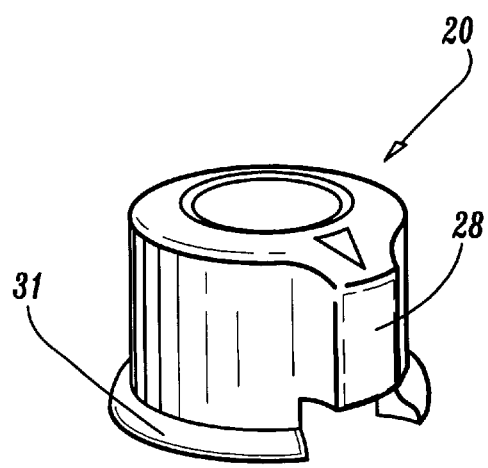
FIG. 19 is a perspective view of the actuating button of the fluid flow valving device formed in accordance with the principals of the present invention.

The core 40 also includes a rectangularly shaped slot 23 which passes through the top surface 24 of the core 40. As can be seen in FIGS. 3 and 7, the slot 23 accommodates the button extension 25 and allows rotation of the button 20 to effect rotation of the core 40 whenever the button 20 is rotated relative to the valve 10. Rotation of the core 40 between the first or open position as shown in FIG. 3, and the lock position shown in FIG. 12, is caused by rotation of the button 20 relative to the valve 10 approximately ninety degrees. The valve 10 may include markings such as on the surface 22 of the upper cap 17 (as shown in FIG. 2) and/or on the button 20 (as shown in FIG. 19), to indicate the position of the core 40 for proper operation of the valve. Also, the surface 22 may include one or more raised surfaces 27 which may interfere with one or more button protrusions 28 (see FIG. 2) to prevent rotation of the button 20 more than ninety degrees. This is an alternative to the vertical slot 61 and nub 62 described above. Similarly, one or more enlarged sections 29 of upper cap openings 21 may be formed to allow the button 20 to move downwardly only when properly aligned therewith. As is readily evident therefor, only a single rotational position of the button 20 allows downward movement thereof, this being the position where the primary fluid flow channel 41 of the core 40 is rotationally oriented for fluid flow with the channels 36 and 39.

Referring to FIGS. 3 and 13–14, a flexible, soft elastomeric spring 30 of generally cylindrical shape is positioned between the button 20 and the top of the valve body 13. The elastomeric spring 30 is held in its position by the seat 35 protruding from the top opening 33 of the conical bore 32. The spring 30 operates to hold the button 20 in its uppermost position where the button shoulder 31 abuts the upper cap 17. The spring 30 also operates to form an air tight seal between the upper extension 34 of the core 40 and the seat 35. The seal includes a sealing surface 44 against the upper extension 34 which allows relative vertical movement of the upper extension 34 therewith without loss of the air tight seal.

When in the actuated position, the fluid flow passage formed by the suction source connector 16, the fluid flow channels 36, 41, 39, and the primary device connector 15, forms essentially an elongate fluid flow channel passing entirely through the valve 10.

As shown in FIGS. 3 and 15–16, the lower cap 14 is covered with the ancillary device connection port cover 19. The cover 19 is formed of a generally cylindrical shape having a diameter preferably equal to the diameter of the lower cap 14 and includes a hinge 45 which may be of the "living hinge" type and formed of polymeric material. The lower cap 14 is preferably attached to the upper cap 17 by a snap fit around the primary device and suction source connectors 15 and 16. However any well known attachment means may be used. As best shown in FIG. 3, the cover 19 includes an integrally formed plug 46 which fits snugly within the bushing opening 48 of the bushing 47 to form an airtight seal.

Figure 17:
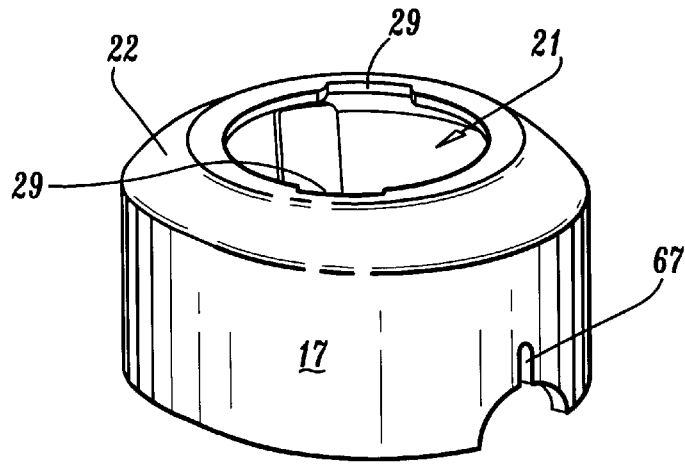
FIG. 17 is a perspective view of the top portion of the housing of the fluid flow valving device made in accordance with the principals of the present invention.
Figure 18:
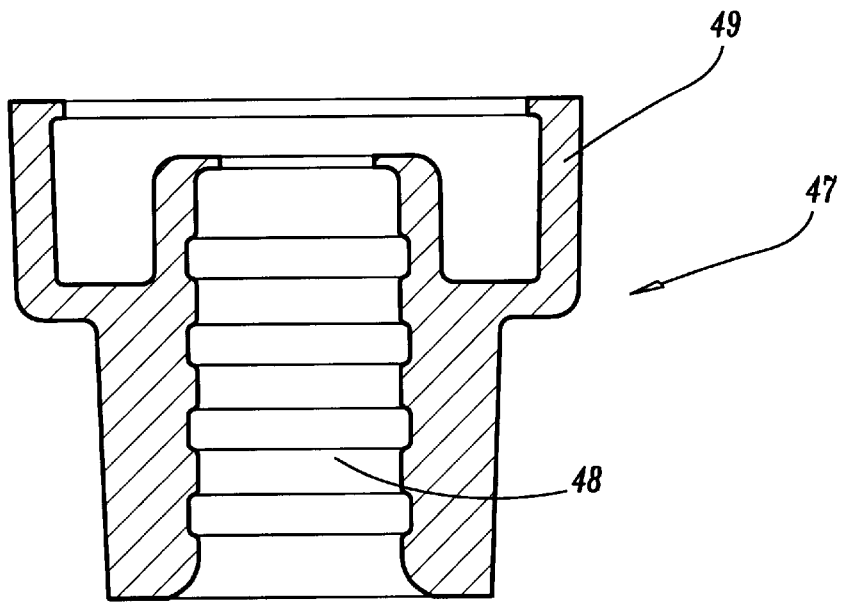
FIG. 18 is a cross-sectional view of the bushing forming the ancillary device connection port of the fluid flow valving device formed in accordance with the principals of the present invention.

As shown in FIGS. 3 and 17–18, the bushing 47 is located within the lower cap 14 between the valve body 13 and the cover 19. The bushing 47 forms the bushing opening 48 therethrough which is shaped on one end thereof to connect with plug 49 on the cover 19 and on the other end to seal with the lower extension 50 of the core 40 in an airtight relationship, thus allowing fluid flow connection of the bushing opening 48 with the suction source through the ancillary fluid flow passage 42 when the core 40 is in the locked position. The bushing 47 also includes a secondary sealing surface 51 which seals against the downwardly extending flange 52 of the valve body 13.

The bushing 47 is preferably formed of a soft polymeric material which can be deformed to accept and hold a relatively rigid connector of an ancillary device, such as the end connector of a Yankauer suctioning wand (not shown).

OPERATION OF THE PREFERRED EMBODIMENT

As shown in FIG. 1, preparation for operation of the valve 10 of the present invention includes attaching the primary device connector 15 thereof to the distal end of a primary device such as the suction catheter device 11, and attaching the suction source connector 16 to a suction tube 13 from a suction pressure source. When it is desired to administer suction to a patient, the suction catheter of the suction catheter device 11 is inserted through the manifold 12 into the patient's trachea or lungs, and the button 20 of the valve 10 is rotated to the "open" position as shown in FIG. 3.

When in the open position, the valve 10 allows a bleed of suctioned atmospheric air to pass into the valve 10 through the upper cap opening 21 and move through the slot 53 of spring 30 (see FIG. 13) into the interior area of the spring 30. The air is then drawn through the bottom space 54 of slot 23 into a bleed by chamber 55 in the upper extension 34 of the core 40. From this position, the air passes through bleed hole 56 and through bleed by extension slot 57 in the primary fluid flow channel 41 and from there through channel 36 and into the suction source connector 16 where it can be drawn out of the valve 10 into the suction pressure source.

Movement of atmospheric air through the valve 10 to the suction source when the button 20 is in the open position generates an auditory signal, being a very recognizable "hissing" sound, which is indicative of the operation of the suction pressure source and the presence of suction pressure within the valve 10.

As shown in FIG. 11, when it is desired to initiate suctioning through the suction catheter device 11, the user forces the button 20 downwardly into the upper cap 17 against the bias of the compression spring 58 and the elastomeric spring 30. This linear translational movement of the button 20 causes the core 40 to move downwardly within the valve housing 13. This causes the primary fluid flow channel 41 of the core 40 to move into vertical alignment with the channels 36 and 39.

As is readily evident, the amount of suction pressure allowed through the fluid flow channel 41 can be regulated from a "no flow" level when the button 20 is released, to gradually increasing flow levels as the fluid flow channel 41 moves downwardly.

Complete depression of the button 20 occurs when the actuation shoulder 59 of the button 20 contacts and seals against the surface 60 of spring 30. In this position, the flow of atmospheric air through the space 54 in slot 23 is blocked. Thus, whenever the button 20 is completely actuated, bleeding of atmospheric air into the primary fluid flow channel 41 is prevented. This causes the "hissing" of the valve 10 to stop, which provides the user with another auditory indication of the proper operation of the valve 10. The user immediately recognizes the absence of the "hissing" sound upon depression of the button 20 as a signal that the suction pressure has been diverted into the suction catheter device 11. In this way, the presence or absence of the "hissing" sound provided by the valve 10 of the present invention assists the user in confirming proper operation of the valve 10.

When the button 20 is released from its actuated position, after suctioning through the suction catheter device 11 is completed, the core 40 moves upwardly again, due to the bias of the compression spring 58 thereagainst, to its open position, and atmospheric air is again allowed to pass through the valve 10 and generate the "hissing" auditory signal. Upward movement of the core 40 is arrested by the abutment of the conical surface 43 thereof with the walls of the conical bore 32 upward movement of the button 20 continues for a small distance due to the bias of spring 30 until it is arrested by the abutment of the shoulder 31 against the upper cap 17.

At times it is convenient, and even important from a safety consideration for a patient, to ensure that depression of the button 20 cannot allow suction pressure through the suction catheter device 11. If it is desired to prevent suctioning through the suction catheter device 11, the user may rotate the button 18, by rotating approximately ninety degrees to the locked position.

As best shown in FIG. 12, ninety degree rotation of the button 20 causes the core 40 to also rotate within the valve body 13 approximately ninety degrees. In this position, the ancillary fluid flow channel 42 is rotationally oriented and vertically aligned with the channel 36. Any incidental depression of the button 20 when in this locked position will fail to allow actuation of the valve 10. Fluid flow through the first fluid flow passage 41 is not possible since it has been moved out of alignment with fluid flow channel 36. Also, the button protrusion 28 is no longer aligned with the enlarged section 29 of the upper cap opening 21 and downward movement of button 20 is prevented. Therefore, no suction pressure can be applied to the suction catheter device 11.

Further, whenever the button 20 has been rotated to the locking position, the bleed by extension slot 57 of the core 40 is also rotated out of alignment with the channel 36. Therefore, bleed of atmospheric air into the primary fluid flow passage 41 is prevented, and the user is aware of such by the absence of the "hissing" auditory signal.

This feature of the present invention allows a user to lock the button 20 against accidental suctioning through the suction device 11 (such as may occur if the valve 10 and suction catheter device 11 are left unattended while attached to a respiratory support system on a patient). Although a patient may inadvertently depress the button 20, for example, by accidentally rolling over on top of the valve 10, suctioning of fluid through the suction catheter device 11 cannot occur since the valve 10 is in the locked position.

Further, medical personnel or other users of the valve 10 will be provided with an auditory signal (absence of hissing) whenever the valve 10 is locked against actuation, and a different auditory signal (the presence of hissing) whenever the valve 10 is unlocked or opened. This can be extremely convenient and add an additional safety factor to the use of the valve 10 in that it is not necessary for the user to see directly whether or not the valve 10 is locked against actuation, because an auditory hissing signal is generated whenever the valve 10 is open, which signals the user that the valve 10 must either be attended to, or rotated to the locked position, in order to avoid possible injury to the patient.

The valve 10 of the present invention may also operate as a connector for an ancillary suctioning device such as a Yankauer suction wand (not shown) if desired. Referring to FIG. 12, when it is desired to attach an ancillary device to the valve 10 of the present invention, the user first places the button 20 in the locked position, then snaps the cover 19 open. The end connector of the Yankauer suction wand or other ancillary device is then inserted through the ancillary device connection port 18 by inserting the suction source end thereof into the bushing opening 48, which generates a friction fit therewith. Attachment of a Yankauer device in this manner provides immediate connection thereof with the suction pressure source attached to the valve 10 through the secondary fluid flow channel 38 and the valve housing fluid flow channel 36.

Attachment of an ancillary device to the valve 10 without requiring detachment of the primary device 11 therefrom can be very important in many procedures involving suctioning of fluids from a patient attached to a respiratory support system. Since serious detriment to the patient can occur whenever it is necessary to breach the integrity of the respiratory support system, the avoidance of disassembly of any equipment thereof, or detachment of the suction source, becomes a positive procedural improvement.

When the Yankauer suction wand is no longer needed, it can be detached from the valve 10 and the cover 19 can again be closed to block the ancillary device connection port 18 and seal it against fluid flow therethrough.

It should be noted that suctioning through the ancillary device connection port 18 of the valve 10 can only be accomplished when the button 20 is in the locked position, with the ancillary fluid flow channel 42 oriented for fluid flow with the fluid flow channel 36.

It should also be noted that all internal components of the valve 10, including the button 20, core 40, body 13, upper and lower caps 17 and 14 respectively, springs 30, and bushing 47 are designed such that assembly thereof is substantially simplified. In each instance, the particular component to be assembled into the valve 10 has been designed to the extent possible to allow each element to fit with each other component only when it is properly positioned for assembly.

For example, the preferred embodiment of the valve 10 of the present invention is assembled by first placing bushing 47 through the opening 26 in the bottom of lower cap 14 until the bushing opening 48 is plugged by cover plug 46 and bushing shoulder 63 rests against the opening 26.

Next, compression spring 58 is placed on top of the bushing 47 and the valve core 40 is placed on top of the compression spring 58 and held in place until the valve body 13 is inserted over the valve core 40 such that the valve core 40 passes through the conical bore 32 thereof. Because of the vertical slot 61 and nub 62 in the valve body 13 and valve core 40 respectively, the valve core 40 is forced to be properly oriented with respect to the valve body 13 when assembled. Prior to seating the valve body 13 in the bottom cap 14, the soft elastomeric spring 30 is positioned in the top opening 33 of the conical bore 32 until the sealing surface 44 thereof seals with the seat 35.

Next, the valve body 13 is inserted into the lower cap 14 until the snaps 64 receive the primary device connector 15 and suction source connector 16. As can be seen in FIGS. 3 and 16, a key 65 extends downwardly from the primary device connector 15 and fits into a slot 66 in the lower cap 14 when the valve body 13 is properly oriented for insertion into the lower cap 14. If the valve body 13 is oriented 180° in the wrong direction, the valve body 13 will not fit into the snaps 64 because of interference with the key 65.

Button 20 is then placed in the upper cap 17 by inserting it through the upper cap opening 21, and the upper cap 17 is attached to the lower cap 14 in a snap fit type attachment. The button extension 25 must be oriented properly to slide into the rectangularly shaped slot 23 on the upper extension 34 of the valve core 40. Because of the protrusions 28 on button 20, the button 20 must be properly oriented in the upper cap opening 21 in order for assembly to be able to be completed. Also, the upper cap 17 includes a slot 67 which receives key 68 on the primary device connector 15 to ensure proper relative orientation of the cap 17 with the remainder of the valve 10.

As can be seen, in this manner, there is only one relative orientation of each and every element in the valve 10 which allows the valve to be assembled.

The valve 10 of the present invention also allows gas sterilization thereof of all the interior surfaces even when the valve is fully assembled. As shown in FIG. 11, when the valve is in the actuated position, a sterilization gas can enter the interior of the valve through channels 36, 39 and upper cap opening 21. Also, when cover 19 is open, gas can pass through opening 48 and channels 38 and 42. When in this position, gas passing through channel 36 can enter the primary fluid flow channel 41 and pass into the bleed-by chamber 55 through bleed hole 56. Gas may flow through channel 39 into the lower portion of conical bore 32, and through upper cap opening 21 into the interior of the soft elastomeric spring 30, and into the general internal cavity area encapsulated by the upper and lower caps 17 and 14 respectively, to thus sterilize the remainder of the internal area of the valve 10 and the valve body 13.

It will be also apparent from the foregoing that, while a particular embodiment of the present invention has been illustrated and described, various modifications can be made thereto without departing from the spirit and scope of the invention. Accordingly, it is not intended that the invention be limited, except as by the appended claims.

What is claimed is:

1. A suction control valve comprising:
   a valve body having a suction source access port, a primary suction device access port, and a fluid flow passage for allowing fluid flow passage between said suction source access port and said primary suction device access port;
   an ancillary suction device access port in fluid flow connection with said fluid flow passage;
   a valve core having a plurality of fluid flow channels formed through a center portion thereof, the valve core being positioned at least partially within said valve body for movement relative thereto between at least a first position in which said primary suction device access port and said ancillary suction device access port are closed against fluid flow therethrough, a second position in which said primary suction device access port is open to fluid flow therethrough and said ancillary suction device access port is closed to fluid flow therethrough, and a third position in which said primary suction device access port is closed against fluid flow therethrough and said ancillary suction device access port is open to fluid flow therethrough;
   a compression spring positioned to bias said valve core against movement thereof to said second position from said first position; and
   an actuation button operably positioned relative to said valve core for moving said valve core from said first position to said second or third positions.

2. A suction control valve according to claim 1 wherein said ancillary suction device access port includes a cap independent of said actuation button for opening and closing said ancillary suction device access port for fluid flow therethrough.

3. A suction control valve according to claim 1 wherein said ancillary suction device access port incudes a relatively flexible bushing forming a fluid flow opening therethrough which is in fluid flow connection with the fluid flow passage, said bushing being held within said valve body by said cap.

4. A suction control valve according to claim 3 wherein said cap includes a cover member hingeably movable between a closed position and an open position, whereby said cover member inhibits fluid flow through said bushing fluid flow opening when in said closed position, and allows insertion of an ancillary suction device into said bushing fluid flow opening when in said open position.

5. A suction control valve comprising:
   a valve body having a suction source connector, a primary suction source device connector, and a fluid flow passage for allowing fluid flow passage between said suction source connector and said primary suction device connector;
   a valve core having a plurality of fluid flow channels formed through a center portion thereof, the valve core being positioned at least partially within said valve body for movement relative thereto between at least a first position in which said primary suction device connector is closed against fluid flow therethrough, and a second position in which said primary suction device is open to fluid flow therethrough;
   a compression spring positioned to bias said valve core against movement thereof to said second position from said first position;
   an actuation button operably positioned relative to said valve core for moving said valve core from said first position to said second or third positions; and
   auditory signal means for producing an auditory signal for indicating the location of said valve core between at least said first and said second positions, said auditory signal means including at least one lead-by opening in said valve core for allowing passage of fluid through said valve body into said fluid flow passage to produce said auditory signal.

6. A suction control valve according to claim 5 wherein said means further includes means for producing said auditory signal to indicate the presence of suction pressure within said fluid flow passage when said valve core is in said first position, and means for stopping production of said auditory signal as said valve core is moved from said first position to said second position.

7. A method of assembling a suction control valve as defined in claim 1 wherein the valve body, the ancillary suction device access port, the valve core, the compression spring, the actuation button, and the elastomeric spring are each formed to be receivable within an upper and lower cap in a single unique orientation, whereby each element must be assembled in the valve in a single unique position, such that improper position of any element therein prevents the completion of the assembly of the valve.

8. A suction control valve according to claim 1 wherein said valve core is rotatable to said third position.

9. A suction control valve according to claim 5 wherein said valve core is rotatable to a locked position which prevents fluid flow through said primary suction device access port.

* * * * *